United States Patent [19]

Yamamoto

[11] Patent Number: 5,843,731
[45] Date of Patent: Dec. 1, 1998

[54] METHOD FOR PURIFYING PLASMID DNA ON CALCIUM PHOSPHATE COMPOUND

[75] Inventor: Akira Yamamoto, Tokyo, Japan

[73] Assignee: Asahi Kogaku Kogyo Kabushiki Kaisha, Tokyo, Japan

[21] Appl. No.: 922,376

[22] Filed: Sep. 3, 1997

[30] Foreign Application Priority Data

Sep. 5, 1996 [JP] Japan ................................. 8-235400

[51] Int. Cl.$^6$ ........................... C12P 19/34; B01D 15/08; B01D 15/04; C01B 15/16
[52] U.S. Cl. ..................... 435/91.1; 210/198.2; 210/692; 423/308
[58] Field of Search ................................. 435/91.1, 306.1; 210/198.2, 656, 691, 692; 423/308; 428/407

[56] References Cited

U.S. PATENT DOCUMENTS

| | | | |
|---|---|---|---|
| Re. 35,267 | 6/1996 | Tsuru et al. ............................. | 210/692 |
| 4,781,904 | 11/1988 | Tagaya et al. ........................... | 423/308 |
| 4,830,969 | 5/1989 | Holmes .................................. | 435/259 |
| 4,952,323 | 8/1990 | Nakabayashi et al. ................. | 210/691 |
| 4,956,298 | 9/1990 | Diekmann ............................ | 435/293.1 |
| 4,981,952 | 1/1991 | Yan ........................................ | 530/384 |
| 5,039,408 | 8/1991 | Ichitsuka et al. ................... | 210/198.2 |
| 5,082,566 | 1/1992 | Tagaya et al. .......................... | 210/656 |
| 5,085,781 | 2/1992 | Tsuru et al. ............................. | 210/692 |
| 5,098,842 | 3/1992 | Nakajima et al. ................... | 435/308.1 |
| 5,208,160 | 5/1993 | Kikyotani et al. ..................... | 435/270 |
| 5,484,720 | 1/1996 | Wurm et al. ......................... | 435/172.3 |
| 5,540,995 | 7/1996 | Kitano et al. ........................... | 428/407 |
| 5,651,884 | 7/1997 | Ichitsuka et al. ................... | 210/198.2 |

OTHER PUBLICATIONS

Colman et al. "Rapid purification of plasmid DNa's by hydroxyapatite chromatography," J. Biochem. (1978) 91: 303–310.

Spencer, M. "Reverse salt gradient chromatography of tRNA on unsubstituted agarose," J. Chromatog. (1982) 238: 307–316.

Lindeberg et al. "High–performance adsorption chromatography of transfer ribonucleic acids and proteins on 2–micron–spherical beads of hydroxyapatite," J. Chromatograph. (1990) 499: 153–165.

Markova et al. "Influence of silver (1+) and mercury (2+) cations on hydroxyapatite chromatography," Anal. Biochem. (1978) 84(2): 633–7.

*Primary Examiner*—Jon P. Weber
*Assistant Examiner*—Susan Hanley
*Attorney, Agent, or Firm*—Greenblum & Bernstein, P.L.C.

[57] ABSTRACT

A method is disclosed for isolating plasmid DNA, having the steps of: suspending hydroxyapatite particles in a buffer solution having a pH of about 6 to about 9, about 1 to about 100 mM of a water-soluble calcium salt and about 1 to about 100 mM of tris(hydroxymethyl) aminomethane; adding a solution containing RNA and plasmid DNA, obtained upon bacteriolysis, to the hydroxyapatite particles-containing suspension, thereby adsorbing the RNA onto the hydroxyapatite particles in the suspension; and recovering the plasmid DNA from a supernatant of the suspension. The isolation method enables effective separation of the purified plasmid DNA from a solution containing RNA and plasmid DNA in a simplified process, without the use for any special separation device.

9 Claims, No Drawings

METHOD FOR PURIFYING PLASMID DNA ON CALCIUM PHOSPHATE COMPOUND

BACKGROUND OF THE INVENTION

1. Field of the Invention

The present invention relates to a method for isolating plasmid deoxyribonucleic acid (DNA) from nucleic acids which is one of the most basic operations in the field of genetic engineering.

2. Description of the Related Art

Hitherto, mass production of a target DNA by integrating and culturing the target DNA into a plasmid vector of *coli* bacteria (*Escherichia coli*) has been widely carried out in the field of genetic engineering.

At present, in the mass production of target DNA, the plasmid vector has been recovered from the *coli* bacteria by conducting bacteriolysis, followed by the removal of the genomic DNA, proteins, etc., to obtain a mixture of ribonucleic acid (RNA) and plasmid DNA. Some well-known methods for the recovery of the plasmid vector include an alkali-SDS (sodium dodecyl sulfate) method, etc. Furthermore, in order to obtain a purified plasmid DNA from the mixture of RNA and plasmid DNA, a column separation method using an ion-exchange resin, a density-gradient centrifugation method using cesium chloride and the like, have generally been used as the separation method.

However, the above-mentioned separation methods have several drawbacks. For example, since the target plasmid DNA is obtained after having been diluted with a voluminous amount of an eluting solution, the column separation method using an ion-exchange resin requires a troublesome concentration of the eluted plasmid DNA. Furthermore, since centrifugation must be carried out in a large scale centrifugal apparatus at a high revolution for a long period of time, the density-gradient centrifugation method requires great care which makes centrifugation troublesome and uneconomical.

SUMMARY OF THE INVENTION

An object of the present invention is to provide an isolation method which enables an effective separation of purified plasmid DNA from a solution containing RNA and plasmid DNA in a simplified process and without the need for any special separation device.

As a result of their diligent studies and research, the inventors of the present invention have found that if a buffer solution containing a calcium salt in a specific concentration, and tris(hydroxymethyl)aminomethane having a specific concentration and a specific pH range is prepared, and the resulting buffer solution is used in the separation of purified plasmid DNA from a solution containing RNA and plasmid DNA, the RNA can be adsorbed on particles of a calcium phosphate compound, however the plasmid DNA is not adsorbed on the same particles. Based upon this finding, the inventors have completed the present invention which will be described hereinafter in detail.

According to the present invention, there is provided a method for isolating plasmid DNA, which includes the steps of:

suspending particles of a calcium phosphate compound having a Ca/P ratio of about 1.0 to about 2.0 in a buffer solution having a pH of about 6 to about 9, about 1 to about 100 mM of a water-soluble calcium salt, and about 1 to about 100 mM of tris(hydroxymethyl) aminomethane to obtain a calcium phosphate particles-containing suspension;

adding a solution containing RNA and plasmid DNA, obtained upon bacteriolysis, to the calcium phosphate particles-containing suspension, thereby adsorbing the RNA onto the calcium phosphate particles in the suspension; and recovering the plasmid DNA from a supernatant of the suspension.

According to the present invention, there is also provided a method for isolating plasmid DNA in accordance with liquid chromatography, which includes the steps of:

filling a chromatographic column with particles of a calcium phosphate compound having a Ca/P ratio of about 1.0 to about 2.0;

equilibrating the column of the calcium phosphate particles with a buffer solution having a pH of about 6 to about 9, about 1 to about 100 mM of a water-soluble calcium salt, and about 1 to about 100 mM of tris (hydroxymetyl)aminomethane;

passing a solution containing an RNA and a plasmid DNA, obtained upon bacteriolysis, and a buffer solution having a pH of about 6 to about 9, about 1 to about 100 mM of a water-soluble calcium salt, and about 1 to about 100 mM of tris(hydroxymethyl)aminomethane, in the described order, through the column; and recovering the plasmid DNA from an eluate of the column.

The present disclosure relates to subject matter contained in Japanese Patent Application No.8-235400 (filed on Sep. 5, 1996) which is expressly incorporated herein by reference in its entirety.

PREFERRED EMBODIMENTS OF THE PRESENT INVENTION

In the practice of the present invention, the particles of a calcium phosphate compound having a Ca/P ratio of about 1.0 to about 2.0 are suspended in the above-described buffer solution or are filled in a chromatographic column. The calcium phosphate compound used herein is not restricted to the one specified, insofar as it has a Ca/P ratio of about 1.0 to about 2.0, and typical examples thereof include one or more members selected from the group consisting of hydroxyapatite, fluoroapatite, tribasic calcium phosphate, tetrabasic calcium phosphate and others, i.e., $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca_4O\,(PO_4)_2$, $CaHPO_4$ and others. Among the above-listed calcium phosphate compounds, it is preferred to use a calcium phosphate compound having a Ca/P ratio of about 1.5 to about 1.8 in view of obtaining a good stability and adsorption property, and more preferably a calcium phosphate compound which contains a hydroxyapatite having a Ca/P ratio of about 1.67 as a principal component thereof. When fluoroapatite is used, it is preferred to adjust the fluorine content in the fluoroapatite to not more than 5% by weight, based on the total amount of the calcium phosphate compounds.

A fluorine content above 5% by weight should be avoided, because it can cause an undesirable dissolution of fluorine from the fluoroapatite. The calcium phosphate compounds can be produced in accordance with any one of the well-known methods.

The particles of a calcium phosphate compound (hereinafter, also referred to as "calcium phosphate particles") used in the present invention preferably have an average particle diameter of about 1 micron($\mu$m) to about 1 millimeter(mm) and a specific surface area, determined in accordance with the BET (Brunauer-Emmett-Teller)

method, of about 1 to about 300 m²/g, and more preferably, about 5 to about 300 m²/g. Regarding the calcium phosphate particles, an average particle diameter of less than 1 µm causes difficulty in the handling of the particles, and a specific surface area of less than 1 m²/g may not ensure a satisfactory adsorptivity due to its low specific surface area. On the other hand, an average particle diameter of more than 1 mm and a specific surface area of more than 300 m²/g can cause a reduction of the filling density and formation of non-uniform aggregate products, respectively, and thus the properties of the particles are deteriorated.

The above-described particles of the calcium phosphate compound can be produced by synthesizing the compound from different types of calcium compounds and phosphoric acid compounds as the starting materials, followed by granulating and drying the obtained calcium phosphate compound and then classifying the dried particles. Sometimes, it becomes necessary to prepare the particles as porous granules in order to obtain particles satisfying the above-described requirements. Such granular calcium phosphate particles can be prepared by using any conventional production method.

In the isolation method according to the present invention, in order to selectively adsorb the RNA of the nucleic acid components onto the above-described calcium phosphate particles, while not adsorbing the plasmid DNA of the same components, a water-soluble calcium salt is added to a buffer solution of tris(hydroxymethyl)aminomethane (hereinafter, referred also to as a "tris buffer solution") to make a tris-buffer solution containing the calcium salt (hereinafter, also referred to as a "tris-calcium salt buffer solution"). To the resulting solution having about 1 to about 100 mM of a water-soluble calcium salt and about 1 to about 100 mM of tris(hydroxymethyl)aminomethane, calcium phosphate particles having a Ca/P ratio of about 1.0 to about 2.0 are added and suspended. Then, to the resulting calcium phosphate particles-containing suspension, a solution containing an RNA and a plasmid DNA obtained upon bacteriolysis, is added. The bacteriolysis can be carried out by using any well-known method such as an alkali-SDS method or the like. Upon the bacteriolysis, genomic DNA of the *coli* bacteria as well as proteins and lipids, i.e., constitutional components of the bacterium body, are removed, thus producing a solution containing principally the remaining plasmid DNA and RNA.

Tris(hydroxymethyl)aminomethane used in the present invention has a concentration of about 1 to about 100 mM. A concentration of less than 1 mM is generally not enough to compensate for a pH of the solution due to the absence of the buffering action, while a concentration above 100 mM can cause adsorption of the plasmid DNA onto the calcium phosphate particles.

Further, in the present invention, about 1 to about 100 mM of a water-soluble calcium salt is present in the buffer solution. Suitable water-soluble calcium salts include, but are not restricted to, calcium chloride, calcium acetate, calcium nitrate and the like. If the concentration of the calcium salt is less than 1 mM, any nucleic acid in the test samples may not be adsorbed onto the calcium phosphate particles, and if the concentration is above 100 mM, adsorption of the plasmid DNA onto the calcium phosphate particles, is possible.

Furthermore in the present invention, the buffer solution containing the water-soluble calcium salt and the tris (hydroxymethyl)aminomethane having the above-described concentration is used at a pH range of about 6 to about 9. A pH of less than 6 causes difficulty in adsorbing the RNA onto the calcium phosphate particles, and a pH of more than 9 can cause an undesirable adsorption of the plasmid DNA onto the particles.

To adjust the pH of the buffer solution containing the calcium salt and tris(hydroxymethyl)aminomethane to be within the above-described pH range, it is preferred to add acid such as hydrochloric acid or like to the buffer solution.

According to the present invention, since the RNA in the nucleic acid components can be selectively adsorbed on the particles of the calcium phosphate compound, and the plasmid DNA can be retained in the tris-calcium salt buffer solution, the plasmid DNA can be easily recovered from the buffer solution by using an alcoholic precipitation method using an alcohol such as ethanol, or by other recovery methods.

Alternatively, the plasmid DNA can be easily isolated from other nucleic acid components by using the above-described particles of the calcium phosphate compound as a filling material in a column for the chromatography, followed by conducting a liquid chromatographic process using the filled column. In the liquid chromatographic process, the plasmid DNA is not adsorbed on the filling material of the column, but is contained in the eluate which will be then discharged from the column.

In carrying out the above chromatographic process, the column is filled with the particles of the calcium phosphate compound and, after equilibration, a test solution containing both the RNA and the plasmid DNA is passed through the column to conduct a separation operation. In this chromatographic process, it is preferred that the tris-calcium salt buffer solution used in the equilibration step and the subsequent separation step has the same concentration and pH value.

The present invention will be further described with reference to working examples thereof. Note, however, that the present invention should not be restricted to these examples.

EXAMPLES 1 TO 11 AND COMPARATIVE EXAMPLES 1 AND 2:

PBulescriptSK(+) (trademark of Stratagene) having an ampicillin-resistant gene was transformed to a JM 109 competent cell which was then cultured in a LB-agar medium containing 50 µg/mL of ampicillin at 37° C. for a whole day and night to obtain a single colony species. The colony species was then cultured by being shaken in an LB culture solution containing 50 µg/mL of ampicillin at 37° C. for a whole day and night to obtain a bacterium body. After centrifugal separation, the bacterium body was treated with an alkali-SDS method to prepare a mixed solution of plasmid DNA and RNA having a nucleic acid concentration of 200 µg/mL (hereinafter, referred to as a "test solution").

A tris-calcium salt buffer solution having a pH, calcium chloride having a concentration and a buffer solution of tris(hydroxymethyl)aminomethane-hydrochloride having a concentration shown in the following Table 1 was prepared.

Thereafter, hydroxyapatite particles having an average particle diameter of about 20 microns and a specific surface area, determined in accordance with the BET method, of about 50 m²/g, were suspended in 70 µL of the tris-calcium salt buffer solution having the described pH, so that a suspension having a concentration of 10% (w/v) was obtained. Then, 10 µL of the test solution was added to 0.2 mL of the obtained suspension and the suspension was shaken for five minutes at room temperature. Thereafter, a supernatant was recovered from the suspension, and then subjected to a gel electrophoretic process using 0.8% agarose gel. An analysis of the nucleic acid components was made with dying using ethidium bromide to obtain the results shown in the following Table 1.

TABLE 1

| Ex. No. | concentration | | | adsorption on | |
|---|---|---|---|---|---|
| | tris-buffer | $CaCl_2$ | pH | hydroxyapatite plasmid DNA | RNA |
| Comp. Ex. 1 | 10 mM | 0 mM | 6 | slightly adsorbed | not adsorbed |
| Ex. 1 | 10 mM | 20 mM | 6 | not adsorbed | adsorbed |
| Ex. 2 | 10 mM | 40 mM | 6 | not adsorbed | adsorbed |
| Ex. 3 | 10 mM | 100 mM | 6 | not adsorbed | adsorbed |
| Comp. Ex. 2 | 10 mM | 200 mM | 6 | adsorbed | adsorbed |
| Ex. 4 | 100 mM | 20 mM | 6 | not adsorbed | adsorbed |
| Ex. 5 | 50 mM | 20 mM | 6 | not adsorbed | adsorbed |
| Ex. 6 | 30 mM | 20 mN | 6 | not adsorbed | adsorbed |
| Ex. 7 | 10 mM | 20 mM | 6 | not adsorbed | adsorbed |
| Ex. 8 | 100 mM | 20 mM | 9 | slightly adsorbed | adsorbed |
| Ex. 9 | 50 mM | 20 mM | 9 | slightly adsorbed | adsorbed |
| Ex. 10 | 30 mM | 20 mM | 9 | slightly adsorbed | adsorbed |
| Ex. 11 | 10 mM | 20 mM | 9 | not adsorbed | adsorbed |

As can be appreciated from the results shown in Table 1, a purified plasmid DNA having a high purity could be obtained using a bufer solution having a pH of 6 to 9, 1 to 100 mM of tris(hydroxymethyl)aminomethane and 1 to 100 mM of calcium chloride.

EXAMPLE 12:

A chromatographic column was filled with hydroxyapatite particles having an average particle diameter of about 20 microns and a specific surface area, determined in accordance with the BET method, of about 50 $m^2/g$, and then the column was washed with a calcium chloride-added tris-buffer solution having a concentration and pH similar to that used in Example 2. Further, a test solution, identical to the mixed solution of plasmid DNA and RNA used in Example 1 was prepared upon bacteriolysis in accordance with the manner described in Example 1.

The test solution and the calcium chloride-added tris-buffer solution in a thrice amount of the capacity of the column were used as an eluting solution, and the eluting solution was passed through the column. The eluting solution was then recovered from the column and subjected to a gel electrophoretic process using 0.8% agarose gel, and then the nucleic acid components were analyzed with dying using ethidium bromide. The presence of the plasmid DNA could be confirmed from the results of the analysis.

According to the isolation method of the present invention, as will be appreciated from the above descriptions, purified plasmid DNA can be easily obtained from a solution containing RNA and plasmid DNA, obtained upon bacteriolysis, in a simplified operation and without the need for any special apparatus. Further, contrary to the prior art methods such as a column separation method using an ion-exchange resin, the isolation method of the present invention can be carried out in a reduced number of operation steps, since an eluting operation is not necessary, and the plasmid DNA can be easily concentrated and purified in accordance with an alcoholic precipitation method or the like.

What is claimed is:

1. A method for isolating plasmid deoxyribonucleic acid, comprising:
    suspending particles of a calcium phosphate compound having a Ca/P ratio of about 1.0 to about 2.0 in a buffer solution having a pH of about 6 to about 9, about 1 to about 100 mM of a water-soluble calcium salt, and about 1 to about 100 mM of tris(hydroxymethyl) aminomethane, to obtain a calcium phosphate particles-containing suspension;
    adding a solution containing ribonucleic acid and plasmid deoxyribonucleic acid, obtained upon bacteriolysis, to said calcium phosphate particles-containing suspension, thereby adsorbing said ribonucleic acid onto the calcium phosphate particles in said calcium phosphate particles-containing suspension; and
    recovering said plasmid deoxyribonucleic acid from a supernatant of said calcium phosphate particles-containing suspension.

2. The method for isolating plasmid deoxyribonucleic acid according to claim 1, wherein the pH of said buffer solution is adjusted by adding acid.

3. The method for isolating plasmid deoxyribonucleic acid according to claim 1, wherein said particles of a calcium phosphate compound have an average particle diameter of about 1 micron to about 1 millimeter and a specific surface area of about 1 to about 300 $m^2/g$.

4. The method for isolating plasmid deoxyribonucleic acid according to claim 1, wherein said water-soluble calcium salt is calcium chloride or calcium nitrate.

5. A method for isolating plasmid deoxyribonucleic acid, comprising:
    filling a chromatographic column with particles of a calcium phosphate compound having a Ca/P ratio of about 1.0 to about 2.0;
    equilibrating said column of the calcium phosphate particles with a buffer solution having a pH of about 6 to about 9, about 1 to about 100 mM of a water-soluble calcium salt and about 1 to about 100 mM of tris (hydroxymethyl)aminomethane;
    loading a solution containing ribonucleic acid and plasmid deoxyribonucleic acid, obtained upon bacteriolysis, and then eluting with a buffer solution having a pH of about 6 to about 9, about 1 to about 100 mM of a water-soluble calcium salt and about 1 to about 100 mM of tris(hydroxymethyl)aminomethane through said column; and
    recovering said plasmid deoxyribonucleic acid from an eluate of said column.

6. The method for isolating plasmid deoxyribonucleic acid according to claim 5, wherein the pH of said buffer solution is adjusted by adding an acid.

7. The method for isolating plasmid deoxyribonucleic acid according to claim 5, wherein said buffer solution of water-soluble calcium salt and tris(hydroxymethyl) aminomethane used in each of said equilibration and separation steps has the same concentration and pH value.

8. The method for isolating plasmid deoxyribonucleic acid according to claim 5, in which said particles of a calcium phosphate compound have an average particle diameter of about 1 micron to about 1 millimeter and a specific surface area of about 1 to about 300 $m^2/g$.

9. The method for isolating plasmid deoxyribonucleic acid according to claim 5, in which said water-soluble calcium salt is calcium chloride or calcium nitrate.

* * * * *